United States Patent [19]
Eibl et al.

[11] 3,960,905
[45] June 1, 1976

[54] DIACYLGLYCEROPHOSPHORIC ACID ESTERS OF AMINOETHANOL AND METHYLAMINOETHANOL AND METHOD OF PREPARING THE SAME

[75] Inventors: Hansjörg Eibl, Bovenden; Alfar Nicksch, Goettingen-Nikolausberg, both of Germany

[73] Assignee: Max-Planck-Gesellschaft zur Förderung der Wissenschaften e.V., Goettingen, Germany

[22] Filed: Aug. 28, 1974

[21] Appl. No.: 501,258

[30] Foreign Application Priority Data
Sept. 6, 1973 Germany.............................. 2345059

[52] U.S. Cl. ................................................. 260/403
[51] Int. Cl.² ............................................ C07F 9/09

[58] Field of Search ..................................... 260/403

[56] References Cited
UNITED STATES PATENTS

| | | | |
|---|---|---|---|
| 2,447,715 | 8/1948 | Rose | 260/403 X |
| 2,864,848 | 12/1958 | McArthur | 260/403 X |
| 3,752,833 | 8/1973 | Aneja et al. | 260/403 |

*Primary Examiner*—Patrick P. Garvin
*Attorney, Agent, or Firm*—Hans Berman; Kurt Kelman

[57] ABSTRACT

Aminoethyl and methylaminoethyl esters of diacylglycerophosphoric acid in which the acyl groups are alkanoyl or alkenoyl having 10 to 22 carbon atoms are prepared in good yield by reaction of the corresponding $\beta$-bromoethyl esters with ammonia or methylamine base.

3 Claims, No Drawings

DIACYLGLYCEROPHOSPHORIC ACID ESTERS OF AMINOETHANOL AND METHYLAMINOETHANOL AND METHOD OF PREPARING THE SAME

This invention relates to diacylglycerophosphoric acid esters of aminoethanol and methylaminoethanol, and to a method of preparing the same.

More specifically, the invention relates to a simple method of preparing glycerophosphatides of the formulas

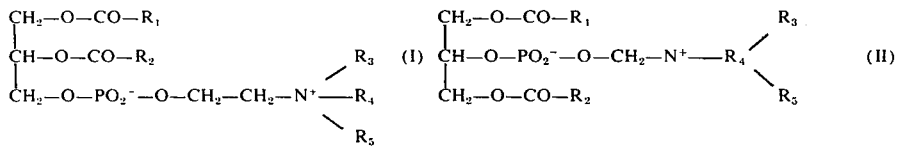

wherein $R_1$ and $R_2$ are alkanoyl or alkenoyl having 9 to 21 carbon atoms, and $R_3$, $R_4$, and $R_5$ are hydrogen or methyl, the same symbols representing the same substituents in all formulas hereinbelow.

The starting materials are 1,2- and 1,3-diacylglycerols of the formulas

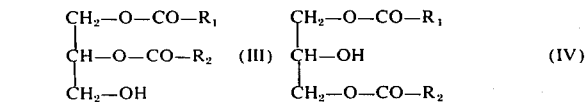

which are reacted with β-bromoethylphosphoric acid dichloride to intermediates of the formulas

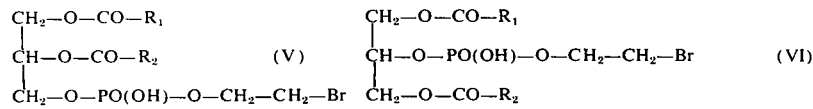

The intermediates readily react with the bases necessary for producing the compounds of Formulas (I) and (II): trimethylamine, dimethylamine, methylamine, and ammonia.

The amination reaction is carried out in a solvent medium consisting of chloroform and at least one member of the group consisting of acetonitrile, nitromethane, an alkanol having up to four carbon atoms, and water. The reaction products, when adequately purified, as by chromatography on silica gel, are white, amorphous powders which cannot be identified by their melting characteristics, but are identifiable by their thin layer chromatograms and by elemental analysis.

They are biodegradable surfactants suitable for use in detergents and as emulsifiers in foods such as margarine. They also have the ability of modifying the properties of cell membranes in a manner to improve the effects of therapeutic agents.

Enzymes in cell membranes contain mixtures of natural phospholipids which include unsaturated aliphatic acid moieties. Because of the instability of these unsaturated moieties in the presence of oxygen, the enzymes are not stable when isolated. When the enzymes are stripped of their natural lipid component, they lose their enzyme activity, but the delipidized enzymes can be reactivated in stabilized condition by mixing them with the compounds of the invention.

It is thought by biologists that hybrid formation and cell fusion are induced by lysolecithin so that cell hybrids may be produced as by Sendai virus. However, the lysolecithins employed in this work are derived from egg lecithin and have substantial cytolytic activity. Cytolysis can be avoided by using compounds of the invention selected for suitable cytolytic activity.

The following Examples are further illustrative of this invention.

EXAMPLE 1

An anhydrous solution of 35 g (0.35 mole) triethylamine in 50 ml chloroform was added with stirring to a solution of 50 g (0.2 mole) β-bromoethylphosphoric acid dichloride in 100 ml anhydrous chloroform cooled with ice. The mixture was transferred to a water bath held at 20°C, and a solution of 50 g (0.1 mole) 1,2-dimyristoylglycerol in 250 ml anhydrous chloroform was added dropwise with stirring. Stirring was continued thereafter at room temperature for 24 hours, whereby the glycerol ester was almost completely consumed as determined by thin layer chromatography.

The reaction mixture was then stirred with an equal volume of ice to decompose the phosphorylation agent, The aqueous phase was discarded, and the separated chloroform layer was stripped of solvent by evaporation. The oily residue was dissolved in 300 ml tetrahydrofuran and further mixed with 60 ml distilled water. The liquid was stirred 60 minutes at 20°C for hydrolyzing residual phosphorylating agent, then mixed sequentially in a separating funnel with 400 ml diisopropyl ether, 400 ml 2% aqueous formic acid, and 100 ml water. The aqueous layer was discarded after thorough shaking, and the diisopropyl ether phase was washed free of formic acid with 400 ml 0.1-molar aqueous sodium acetate solution and 100 ml methanol. It was then stirred 30 minutes with 20 g desiccated sodium sulfate, and the solvent was evaporated. The residue was a yellow oil which was taken up in 450 ml methanol.

The solution was cooled to 0°–5°C and stirred 15 minutes with 15 g active carbon. It was then filtered, and the filtrate was diluted to 600 ml with methanol. It was found to contain 52 g practically pure 1,2-dimyristoyl-glycero-3-phosphoric acid β-bromoethyl ester suitable as an intermediate for further reactions without purification. The methanol solution could be stored in a refrigerator for several months without showing evidence of decomposition.

EXAMPLE 2

7 g (0.01 mole) of the intermediate prepared in Example 1 was dissolved in 100 ml chloroform, and the solution was mixed with 100 ml acetonitrile in a 500 ml round-bottom flask. 60 ml Trimethylamine dissolved in 120 ml ethanol was added, and the resulting reaction mixture was stored in the well stoppered flask for 24 hours at 25°C. Thereafter, the solvent was evaporated, and the residue was mixed with 100 ml chloroform, 120 ml methanol, and 100 ml 2% aqueous formic acid solution and shaken thoroughly. The chloroform phase was washed in a separating funnel with 100 ml 0.1-molar, aqueous sodium acetate solution and 120 ml methanol to remove formic acid, then dried by stirring 10 minutes with 10 g sodium sulfate. After evaporation of the solvent from the dried solution, the residue was recrystallized from 100 ml ethylmethylketone. The yellowish crude product so obtained weighed 6 g. It was purified by chromatography on silica gel and subsequent recrystallization from ethylmethylketone, whereby 5.3 g pure, white choline 1,2-dimyristoyl-glycero-3-phosphate was obtained (62 % yield, based on dimyristoylglycerol).

EXAMPLE 3

7 g (0.01 Mole) intermediate prepared in Example 1 was processed as in Example 2, 60 ml dimethylamine being substituted for the equal volume of trimethylamine under otherwise unchanged conditions.

4.8 g Pure 2-dimethylaminoethyl 1,2-dimyristoyl-glycero-3-phosphate (58% yield based on dimyristoylglycerol) was obtained as a white powder.

EXAMPLE 4

7 g (0.01 Mole) of the intermediate prepared in Example 1 was dissolved in 200 ml chloroform, and the solution was mixed sequentially with 200 ml acetonitrile, 40 ml methanol, and 55 ml methylamine in the form of its 40% solution in ethanol. The reaction mixture was stored in a stoppered flask for 24 hours at 25°C, and was then worked up as described in Example 2.

2-Methylaminoethyl 1,2-dimyristoyl-glycero-3-phosphate was obtained as a pure powder in an amount of 4.5 g (54% yield, based on dimyristoylglycerol).

EXAMPLE 5

7 g (0.01 Mole) of the intermediate obtained in Example 1 was dissolved in 50 ml chloroform, and the solution was mixed sequentially in a 1-liter round-bottom flask with 100 ml acetonitrile, 100 ml methanol, and 100 ml ammonia (25% aqueous solution). The reaction mixture was heated to 49°C and worked up after 24 hours at this temperature as described in Example 2. After purification by chromatography, pure 2-aminoethyl 1,2-dimyristoyl-glycero-3-phosphate was obtained in an amount of 4.2 g (53% yield, based on dimyristoylglycerol).

When 1,2-dimyristoylglycerol was replaced in the procedure of Example 1 by 1,3-dimyristoylglycerol, 1,3-dimyristoyl-glycero-3-phosphoric acid $\beta$-bromoethyl ester was obtained as an intermediate, and was converted to 2-aminoethyl 1,3-dimyristoyl-glycero-3-phosphate and its N-methyl substitution products in the manner of Examples 2 to 5 in comparable yields.

The 1,2- and 1,3-acyl-glycerols in which acyl was alkanoyl or alkenoyl having 10 to 22 carbon atoms reacted in substantially the same manner with $\beta$-bromoethylphosphoric acid dichloride as described above with reference to 1,2-dimyristoylglycerol, and the intermediates so formed could be substituted successfully for the intermediate specifically referred to in the procedures of Examples 2 to 5. The 1,2- and 1,3-acyl-glycerols employed as starting materials are prepared in a known manner (see Slotboom et al. Chem. Phys. Lipids 5 [1970] 301–398).

What is claimed is:

1. A method of preparing a diacyl-glycerophosphoric acid ester of $\beta$-amino-ethanol or N-methyl-$\beta$-amino-ethanol which comprises reacting a diacyl-glycerophosphoric acid ester of $\beta$-bromoethanol with a base of the formula $NH_2R$ in a liquid solvent medium until said ester of $\beta$-amino-ethanol or N-methyl-$\beta$-amino-ethanol is formed, in said formula R being hydrogen or methyl, acyl in said diacyl being alkanoyl or alkenoyl having 10 to 22 carbon atoms.

2. A method as set forth in claim 1, wherein aid solvent medium essentially consists of chloroform and at least one member of the group consisting of acetonitrile, nitromethane, methanol, ethanol, and water.

3. A method as set forth in claim 2, wherein said ester of $\beta$-bromoethanol is reacted with an excess of said base.

* * * * *